United States Patent [19]
Restrepo et al.

[11] Patent Number: 6,150,409
[45] Date of Patent: *Nov. 21, 2000

[54] ADJUVANTS AND METHODS FOR RAISING INTRACELLULAR CALCIUM ION CONCENTRATION

[75] Inventors: Diego Restrepo, Littleton, Colo.; George Gomez; Gary K. Beauchamp, both of Philadelphia, Pa.; Masahiro Tanida, Kanagawa-ken, Japan; Tsutomu Saito, Tokyo-to, Japan; Shoji Nakamura; Yoshirou Okazaki, both of Kanagawa-ken, Japan; Shinichi Wachi, Tokyo-to, Japan; Yasuhiro Takashima, Kanagawa-ken, Japan

[73] Assignees: Monell Chemical Senses Center, Philadelphia, Pa.; Takasago International Corporation, Japan; Sheseido Co., Ltd., Japan

[*] Notice: This patent issued on a continued prosecution application filed under 37 CFR 1.53(d), and is subject to the twenty year patent term provisions of 35 U.S.C. 154(a)(2).

[21] Appl. No.: 09/177,919

[22] Filed: Oct. 23, 1998

[51] Int. Cl.⁷ .................................................. A61K 31/44
[52] U.S. Cl. ............................................. 514/535; 514/537
[58] Field of Search ........................................ 514/535, 537

[56] References Cited

U.S. PATENT DOCUMENTS

| | | |
|---|---|---|
| 4,294,266 | 10/1981 | Sprecker et al. |
| 4,790,990 | 12/1988 | Mason et al. .............................. 424/438 |
| 5,672,352 | 9/1997 | Clark et al. ............................... 424/405 |

OTHER PUBLICATIONS

Cain, W.S., et al., "Olfactory adaptation as an aspect of odor similarity,"*Chemical Senses,*1992, 17(5), 481–491.

Lowry, L.D., et al "Experimental cell biology of taste and olfaction."Speilman, A.I. et al. (eds.), 1995, 47–48.

Restrepo, D., et al., "Human olfactory neurons respond to odor stimuli with an increase in cytoplasmic $Ca^{2+}$," *Biophys. J.,*1993, 64(6), 1961–1966.

Rawson, N.E., "Selectivity and response characteristics of human olfactory neurons", *J. Neurosci.,* 1997, 1606–1613.

Schild, D., et al., "Transduction mechanisms in vertebrate olfactory receptor cells,"*Physiol. Rev.,*1998, 78(2), 429–466.

Kawai et al., "Olifactory organ,"1996, 47(5), 482–485.

Kurahashi, et al, "Second messenger in the olfactory transduction,"*Nat. Inst. Physiol. Sci.,* 1 271–275, 1992.

*Primary Examiner*—Rebecca Cook
*Attorney, Agent, or Firm*—Woodcock Washburn Kurtz Mackiewicz & Norris LLP

[57] ABSTRACT

Adjuvants for preventing adaptation to odors comprising one or compounds having the following formula (1):

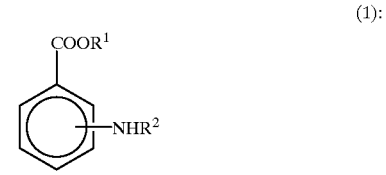

wherein R1 is a C1 to C8 lower alkyl group or a C7 to C9 aralkyl group, and R2 is a hydrogen atom or a C1 to C8 lower alkyl group, are described, as are compositions containing the same, and methods for preventing the adaptation to odors. Methods for increasing intracellular calcium ion levels and for prolonging the sensory response of chemoreceptive cells also described.

4 Claims, 8 Drawing Sheets

1 = MYRACALDEHYDE
2 = CEDRYL METHYL ETHER
3 = CITRONELLOL
4 = COUMARIN
5 = CYCLAMEN ALDEHYDE
6 = ETHYL-2-2-6-TRIMETHYL CARBOXYLATE
7 = HALLONAL
8 = SANTALEX
9 = TONALIDE

ADJUVANTS AND METHODS FOR RAISING INTRACELLULAR CALCIUM ION CONCENTRATION

FIELD OF THE INVENTION

The present invention relates to adjuvants for raising the concentration of intracellular calcium ions and, more specifically, to adjuvants for reducing adaptation to odors. Raising the intracellular calcium ion concentration in olfactory receptor neurons affects odor adaptation, or the decreased ability to sense odors subsequent to initial exposure. The adjuvants of the present invention maintain intracellular calcium ion concentration at a high level, thereby preventing adaptation to odors and, thus, permitting the odors to be sensed for a prolonged period of time.

BACKGROUND OF THE INVENTION

Conventionally, odors have affected human lives in various ways. Many researchers have been interested in, and have studied, why and how odors can be sensed, and have presented results in interpretive articles, reports, etc. on the study of odors. Although some theories about odors have been developed therein, it cannot be said that there is an established theory capable of elucidating the phenomena of odors and being applicable widely to such phenomena.

The adaptation to odors, i.e., the sensing of odors strongly at first but diminishing over time, is one such phenomenon that has heretofore not been fully elucidated. For example, the adaptation to odors such as anethole, ethyl n-butyrate, 2,3-pentanedione, and others was examined in *Chemical Senses*, Vol. 17(5): 481–491 (1992), but no theory of adaptation to these odors has been set forth.

The adaptation to odors is often inconvenient, if not dangerous, for humans because odors cannot be sensed in spite of the fact that the odors are not dispersed and the odor-emitting substance still remains. Therefore, attempts have been made to prevent the adaptation to odors in order to permit the odors to be sensed for a prolonged period of time. For example, one approach involves the intermittent exposure of odors to test subjects. This approach consists of exposing the subject to an odor-emitting substance for a predetermined period of time, suspending the exposure for a predetermined period of time, and then re-exposing the subject to the odor-emitting substance. However, the controlled release of odors cannot be monitored continuously, so this approach does not provide an effective, nor practical, solution.

Another approach is known in which the subject is exposed to a first odor-emitting substance and then to a second, different odor-emitting substance. In this approach, the adaptation to the first odor is terminated by sensing the second odor. However, the second odor cannot always be sensed, and it is difficult to select the second odor substance because the second odor substance affects the sense of the first odor. Thus, this approach is not satisfactory. Further, the same odor cannot be sensed continuously, so this approach does not provide an effective, nor practical, solution either.

SUMMARY OF THE INVENTION

In one aspect, the present invention provides an adjuvant for odor-emitting substances, or a composition containing the adjuvant, that diminishes adaptation to the odors emitted therefrom.

In another aspect, the present invention provides compositions containing odor-emitting substances such as perfumes, cosmetics, or aromatics, detergents, bath additives or air care products containing the adjuvant, or a composition containing the adjuvant.

In yet another aspect, the present invention provides a method for preventing the adaptation to odors, permitting the odors to be sensed for an extended period of time.

In a further aspect, the present invention provides a method for raising/maintaining the concentration of intracellular calcium over basal levels for a prolonged period.

In yet a further aspect, the present invention relates to a method for prolonging the sensing of a stimulus in chemoreceptive cells.

DETAILED DESCRIPTION OF THE INVENTION

Figure 1:
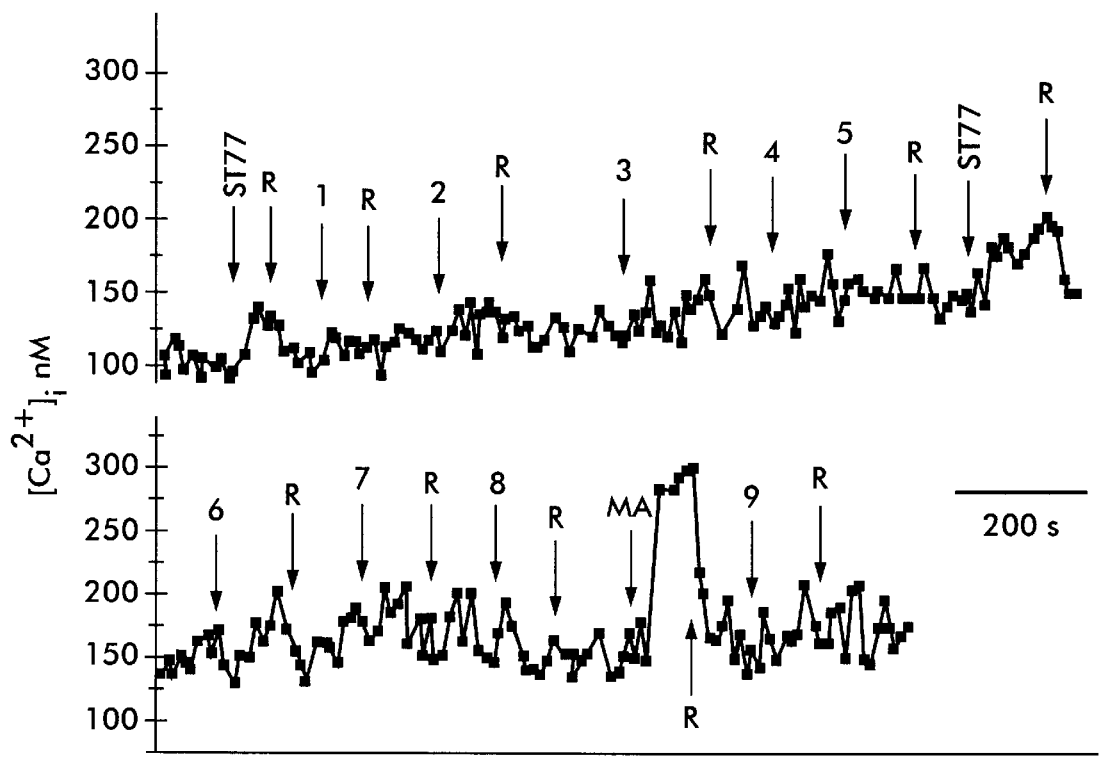
FIG. 1 identifies methyl o-aminobenzoate (methyl anthranilate (MA)) as the active component in Mix ST-77, which we have shown to increase the calcium ion concentration in olfactory cells.

Hereinafter, the present invention is described in more detail. Although the invention is described specifically by reference to the sensing of odor through ciliated olfactory receptor neurons, the adjuvants and methods according to the invention can be extended to any chemoreceptive cells (e.g., taste cells, microvillar olfactory cells, somatosensory cells, vomeronasal cells, trigeminal neurons, cultured cells) in which the raising/maintaining of high intracellular calcium ion concentration correlates with a prolonging of the sensory response. By "prolonging the sensory response" is meant the extension of the period of time a stimulus is sensed by the aforementioned cells as compared to when the adjuvants are not present.

As used herein, the term "target cells" refers to chemoreceptive cells in which the raising/maintaining of high intracellular calcium ion concentration correlates with a prolonging of the sensory response, including, but not limited to, olfactory cells.

As used herein, the term "contacting" refers to the exposure of chemoreceptive cells to adjuvants according to the invention by any means including, without limitation, intranasally and orally.

As used herein, the term "subject" refers to humans and other mammals, birds, fishes, amphibians, reptiles, and other vertebrates As used herein, the term "odor-emitting substance" refers to substances which emit odors that can be sensed by humans and/or other vertebrates.

As used herein, the term "about" means ±10%.

As used herein, the term "adjuvant" refers to a compound (s) to be used in combination with another substance, e.g., an odor-emitting substance, wherein the response to the other substance is enhanced either in strength or duration as compared to the response when the compound is not present.

During the process of odor sensation, the olfactory cells that are present in the olfactory epithelium detect odor molecules. The surface of the olfactory epithelium is covered with mucous secreted from the Bowman's gland. Odor molecules become dissolved in this mucous, facilitating their contact with the olfactory cells. The site of contact of the odor with the receptor cell is at olfactory receptor proteins.

The olfactory cells exhibit a resting membrane potential of −30 to −70 mV. Upon stimulation with odors, stimulation of the olfactory receptor proteins elicits, through a biochemical cascade, a graded depolarization of the olfactory receptor cell. This depolarization, termed the receptor potential, elicits an increase in the frequency of firing of regenerative action potentials that travel along the axon to the olfactory bulb. If the concentration of odors is increased, the amplitude of the receptor potential is increased eliciting a further increase in the frequency of action potential firing.

The olfactory cells present in the nasal mucous membrane extend a dendrite that terminates in a structure called the olfactory vesicle or knob from which extend thin cylindrical processes called cilia. These cilia, which are bathed in the mucous covering the olfactory epithelium, are where odors come in contact with olfactory receptor proteins. All the other proteins necessary for generation of the receptor potential (e.g. cAMP-gated channel, adenylyl cyclase, $G_{olf}$) are located in these cilia. Experiments using biochemical, molecular biological, electrophysiological, and biophysical techniques implicate the second messenger cAMP as a second messenger mediating olfactory transduction. Upon stimulation of olfactory receptors, the G-protein $G_{olf}$ stimulates adenylyl cyclase causing an increase in the concentration of the second messenger cAMP. The increase in cAMP concentration elicits opening of a cAMP-gated cation channel mediating an influx of $Ca^{2+}$. The subsequent increase in intracellular $Ca^{2+}$ causes opening of $Ca^{2+}$-activated $Cl^-$ channels eliciting cell depolarization (the receptor potential). Other mechanisms for mediation of the odor response have been described, but are not as well-established as the cAMP cascade.

The initial process of distinguishing odors in olfactory cells consists of two processes of chemo-electrical signal transformation for first detecting odor molecules and then generating receptor potentials, followed by the transformation of analog information into digital information for the transformation from receptor potentials to neuron impulses or action potentials in neuron axons in the same cells. The transmission and conversion of action potential information into the olfactory bulb (central nervous system) is similar to the mechanism found in most post-synaptic nerve cell interactions. The exchange of information in odor reception is cosidered to be carried out by various well-controlled functional molecules in time/space in olfactory cells.

The ability of olfactory cells to distinguish odors is determined by the specificity of ligands to receptor proteins, similar to the receptor system such as neurotransmitters. Indeed, part of a gene group considered to code for an odor receptor protein has been identified. The mechanism of signal amplification for explaining high sensitivity is elucidated by the involvement of a second messenger due to the cAMP system and inositol triphosphate ($IP_3$) system, both of which are chemical signal amplification systems in cells, and by involvement of $Ca^{2+}$ dependent $Cl^-$ channels.

The response of isolated olfactory cells to odors gradually decreases, however, even though stimulation continues. This decrease occurs because the biochemical cascade and the channels, which opened upon stimulation with the odor substance, are slowly inactivated even in the presence of the stimulating substance. We wished to inhibit this phenomenon, which is called olfactory adaptation.

Odor-induced changes in intracellular calcium are an indirect measure of cAMP-gated channel activity that can be employed to measure responses to odors in the behaviorally relevant time range. We reasoned that some odor compounds that in perfumery's lore are thought to slow adaptation might have an effect on intracellular $Ca^{2+}$ concentration.

In order to test this hypothesis, odor induced changes in intracellular $Ca^{2+}$ were measured in human olfactory neurons in response to two odorant mixtures that had been chosen by perfumers as fast-adapting (ST-AD) and slow-adapting (ST-77). Consistent with our hypothesis, ST-AD showed adaptation in the $Ca^{2+}$ assay while ST-77 displayed a sustained increase in $Ca^{2+}$.

A study of the main components of ST-77 identified methyl anthranilate as the active component. Surprisingly, ST-77 elicited an increase in intracellular $Ca^{2+}$ by what appears to be a nonspecific effect on the membrane. In essence, MA acts as a volatile $Ca^{2+}$ ionophore. When sub-threshold amounts of MA were added to the cell, other odorants would elicit a response that was not otherwise detectable.

Although odor adaptation depends strongly upon $Ca^{2+}$ ions, it does so in often contradictory manners (for a thorough discussion, see *Taisha,* Vol. 28, Extra Issue, page 271 (1991); *Seitai No Kagaku,* Vol. 47, No. 5, page 482 (1996); and Schild and Restrepo, *Physiol. Rev.,* 78:429–466, 1998.). For example, in the absence of detectable extracellular $Ca^{2+}$ ions, inactivation of the odor response measured electrophysiologically in single olfactory neurons in the time range from 0 to a few seconds does not occur, and even if extracellular $Ca^{2+}$ ions are present, the inactivation rarely occurs if intracellular $Ca^{2+}$ ions are maintained low by introducing EGTA into the cells. On the other hand, our investigations have shown that inhibiting protein kinases A and C leads to sustained elevation in intracellular $Ca^{2+}$. Although these enzymes were previously shown to be activated by odor stimulation and to play a role in signal termination, either by inactivating the ion channels or activating the enzymes that break down the odorant-receptor complex, the role of these signal termination events in odor adaptation, much less the role of protein kinases A and C, was not known.

Therefore, although it is clear that intracellular $Ca^{2+}$ affects olfactory adaptation, it does so in a complex manner, and our understanding of the action of $Ca^{2+}$ on olfactory adaptation is not yet complete.

To confirm the reduction in adaptation to odors, we tested MA and MA derivatives for their effect on olfactory adaptation using psychophysical measures. As presented herein, it was found that, when added as an adjuvant, MA and MA derivatives inhibited olfactory adaptation to single odor-emitting substances and to mixtures of odor-emitting substances. Accordingly, we hypothesized that the adaptation to odor occurs by modification of the information exchange system with the introduction of $Ca^{2+}$ into cells and that, if intracellular calcium ion concentrations could be maintained at high levels, adaptation would be prevented.

As mentioned above, to prevent adaptation, we focused upon maintaining intracellular $Ca^{2+}$ concentration at an elevated level for an extended period of time. Increases in intracellular calcium ion concentration in olfactory cells upon stimulation with odor-emitting substance had been reported previously (see, for example, Biophys. J., 64: 1961–1966, 1993). We found, however, that certain substances, specifically volatile amino-benzoates, can not only raise the calcium ion concentration in olfactory cells, but can also maintain the raised calcium ion concentration for a prolonged period of time (e.g., 10 to 15 minutes). Further, these substances can prevent adaptation of another odor-emitting substance (as measured in a psychophysical assay) when used in combination with such odor-emitting substance. This ability of volatile aminobenzoate compounds to retard adaptation, i.e., maintain intracellular $Ca^{2+}$ at elevated levels, is the main premise of the present invention. Although aminobenzoates are specified, other compounds having similar effect are within the scope of the present invention.

The fact that MA elicits a sustained elevation in intracellular $Ca^{2+}$ does not unequivocally imply that MA causes a slowing of olfactory adaptation. However, we assert that levels of intracellular $Ca^{2+}$ may be used as a metric to predict the effectiveness of a compound to reduce adaptation. This provides us with a useful tool for the design and implementation of MA and MA analogs in creating slow adapting odors and fragrances.

Aminobenzoates are known to be repellents in rodents and in birds. (See for example, U.S. Pat. Nos. 4,790,990, 5,464,625, and 5,672,352 (incorporated by reference herein in their entireties). It was not previously known, however, that these substances raise intracellular calcium ion concentration and maintain it at a high level; nor were there any reports that these substances, or any other substances for that matter, prevented the adaptation to odors. Hence, the invention described herein elucidates the previously unknown mechanism of inhibition of odor adaptation by volatile aminobenzoate compounds.

Both adjuvants and methods for permitting the raising and maintaining of calcium ion concentration in cells, particularly olfactory cells, are disclosed herein.

The adjuvants according to the present invention consist of compounds of formula (1):

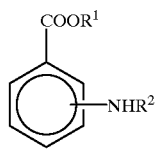

In this compound, R1 is preferably a C1 to C8 lower alkyl group such as a methyl group, ethyl group, etc. or a C7 to C9 aralkyl group such as a phenylmethyl group, phenylethyl group, or phenylpropyl group; R2 is preferably a hydrogen atom, or a C1 to C8 lower alkyl group such as a methyl group, ethyl group, etc.

The compounds of formula (1) are preferably methyl o-aminobenzoate (methyl anthranilate), ethyl o- or m-aminobenzoate (ethyl anthranilate), methyl o-N-methylaminobenzoate (methyl N-methyl anthranilate), benzyl o-aminobenzoate, phenylethyl o-aminobenzoate (phenylethyl anthranilate) and phenylpropyl o-aminobenzoate (phenylpropyl anthranilate).

The amount of the above aminobenzoate derivatives necessary to raise and maintain the calcium ion concentration in cells varies depending on the compounds used, the target cells, and the species from which the target cells were obtained. However, an amount from about 1 $\mu$M to several tens of mM, preferably from about 500 $\mu$M to 1 mM, is contemplated. In contrast, when the aminobenzoate derivatives are used as adjuvants, the amount of the aminobenzoate derivatives necessary to raise and maintain intracellular calcium levels is about 0.5 $\mu$M to about 10 $\mu$M.

The compounds of formula (1) may be used singly or in combination of 2 or more compounds. In preferred embodiments, the combination comprises a mixture of methyl o-aminobenzoate and at least one member selected from methyl m-aminobenzoate, ethyl o-or m-aminobenzoate, phenylethyl o- or m-aminobenzoate, benzyl aminobenzoate, and phenylpropyl o- or m-aminobenzoate. If methyl o-aminobenzoate is to be combined with another compound, the mixing ratio is preferably from about 100:1 to 1:100. In particular, it has been found that the ratio of 50:50 exhibits synergistic effects.

The application of the present invention is not limited to humans, but also includes mammals, birds, fishes, amphibians, reptiles, and other vertebrates. The base, i.e., pre-stimulation, calcium ion concentrations between different target cells from the same preparation and between different species of animals varies, but can be readily obtained by one skilled in the art as described below. Base calcium concentrations in most viable olfactory cells, however, ranges from near zero to about 250 nM.

The maintenance of the calcium ion concentration at a high concentration herein refers to the increase of the calcium ion concentration by at least 10% of the baseline value and/or the increase in the decay constant for the response (t ½) by at least 10%. The decay constant (t ½) is the time required for the response to decrease (decay) to 50% of the maximum increase in calcium ion concentration reached after addition of the fragrance, adjuvant, or mixture.

Adaptation time varies depending upon the odor-emitting substance, its concentration, and the subject. Thus, the period of time during which the calcium ion concentration is maintained at high concentration by the adjuvants of the present invention will vary concomitantly, but will usually be in the range of from about a few seconds to about 20 minutes. As will be evident from the following description and Examples, the odor of an odor-emitting substance can be sensed while the high concentration is maintained.

Several methods are known for measuring calcium ion concentration. Any method will be suitable. The measurements described below were carried out in accordance with the method reported in *Biophys. J.*, 64:1961–1966 (1993), incorporated herein by reference in its entirety. Briefly, $Ca^{2+}$ levels in olfactory cells are measured using the $Ca^{2+}$-sensitive fluorescent pigment fura-2. Cells with fura-2 in their cytoplasm are illuminated with 340 nm UV light, and fura-2 that is bound to intracellular calcium emits light at 510 nm; fura-2 fluoresces more intensely in the presence of calcium. Cells are then illuminated with 360 nm UV light, which excites all the fura-2 present in the cell. The ratio of the intensity of 510 nm light emitted by fura-2 at 340 and 360 nm illumination gives an indirect measure of calcium concentrations within the cell.

In the widely used microscopic fluorescent imaging measurement system, the separation of the excitation light from the fluorescent light is carried out by an interference filter and a dichroic mirror. To determine the strength of fluorescence, the image element output of 8 screens in total in a window of 5×5 image elements by a charged-coupled device camera is summed up and recorded at ⅓-second intervals.

The objective measurement of adaptation was determined as follows. Isolated cells were situated in a chamber on an optically clear surface. Cells were stimulated with odors by dissolving an odor-emitting substance in normal Ringer's solution (which contains 1 mM calcium) and exchanging the bathing Ringer's solution with the odor substance-containing Ringer's solution through perfusion. Cells that responded to the application of the odor with a change in intracellular calcium concentrations could be visually monitored by the changes in fluorescence intensity. The effects of a solution of a reaction reagent (adjuvant) for the odor-emitting substance can then be monitored in a similar fashion.

The subjective measurement of the adaptation to odors in an organoleptic evaluation test was judged in the following manner. A continuous flow of an odor-emitting substance at a predetermined concentration was evaluated for a change in strength of its odor at 30-second intervals for 15 minutes by perfumers skilled in the art. If the above adjuvants, or a mixture thereof, are used in conjunction with an odor-emitting compound or composition, such as perfumes, cosmetics, etc., the adaptation to the odors produced by said compounds or composition is prevented and the odors can be sensed for a prolonged period of time.

The present invention is not limited to the odors derived from the adjuvant compounds described above, but also includes odors generally perceived as pleasant such as, for example, perfumes, cosmetics, bath additives, aromatics, detergents, air care products, foods, and other compounds or compositions, as well as odors generally perceived as unpleasant. By use of the present adjuvants, the following effects can also be achieved—it is possible to secure safety by preventing adaptation to harmful odors, for example, town gas, rotten foods, and poisonous substances, etc. Additionally, if the adjuvants are introduced into a repellent, the repellent's effect can be maintained continuously.

The amount of the adjuvant(s) of the present invention that is needed to raise and maintain the calcium ion concentration in olfactory cells varies depending on the type of compound used, whether or not a mixture of compounds is employed, and the source of the target cells. By itself, the adjuvant is effective at concentrations of from about 0.05 mM to about 1 mM in raising and maintaining intracellular calcium in human olfactory cells, but it is effective at lower concentrations—e.g., 0.5 μm to 10 μm—when used as an adjuvant to assist the effectivity of other compounds. The concentration of the adjuvant in the final composition must, of course, be greater than in the experiments with isolated olfactory neurons because a) only a small quantity of the adjuvant becomes volatile; b) diffusion of adjuvant in the air lowers the effective concentration; and c) only a small amount of adjuvant reaches the olfactory neurons due to the partition of the adjuvant into the mucous layer.

The adjuvants according to the present invention enable intracellular calcium ions to be maintained at high concentration, thereby preventing adaptation to odors. A composition containing an odor-emitting substance and an adjuvant according to the present invention permits the odors of both the adjuvant and the odor-emitting substance to be sensed for a prolonged period of time before adaptation to the odors. If the above adjuvant is incorporated into an aromatics, bathing additives, detergents, air care products etc., its odors can be sensed similarly for a prolonged period of time.

EXAMPLES

Hereinafter, the present invention is described in more detail with reference to the following examples which are not intended to limit the scope of the present invention.

Calcium ion concentration was determined in the method described above. Apparatus used for analyses include the Xenon fluorescent lamp, Nikon diaphot microscope with a fluor 40×1.3 n.a. objective; OPELCO KS-1380 image intensifier with a Sanyo CCD camera; and Quantimet 570 image analysis workstation (Leica, Inc.) The aminobenzoates used in the following experiments were obtained from Aldrich.

Example 1

Olfactory cells from a healthy person were obtained by a biopsy procedure (Lowry LD and EA Pribitkin, *Experimental Cell Biology of Taste and Olfaction*, Spielman AI and JG Brand, eds., pp. 47–48, 1995, incorporated herein by reference). Individual neurons were isolated in a usual manner and immersed in Ringer's solution (Restrepo, D. et al. *Biophys. J.* 64:1961–1966, 1993, incorporated herein by reference). Either the active Mix ST-77, or the individual components thereof, i.e., methyl o-aminobenzoate (methyl anthranilate, MA), myracaldehyde, cedryl methyl ether, citronellol, coumarin, cyclamen aldehyde, ethyl 2,2,6-trimethylcyclohexanecarboxylate, Heliobouquet, Santalex, or Tonalide, was added to Ringer's solution via superfusion (flowing the solutions over the neurons). Each component was mixed at 0.03 μl pure odor-emitting substance per 1 ml Ringer's. The change in the intracellular calcium ion concentration over time was examined. The results are shown in FIG. 1. Mix ST-77 raised intracellular calcium ion concentration. From these results, the active component in Mix ST-77 was identified as MA.

Example 2

Figure 2:
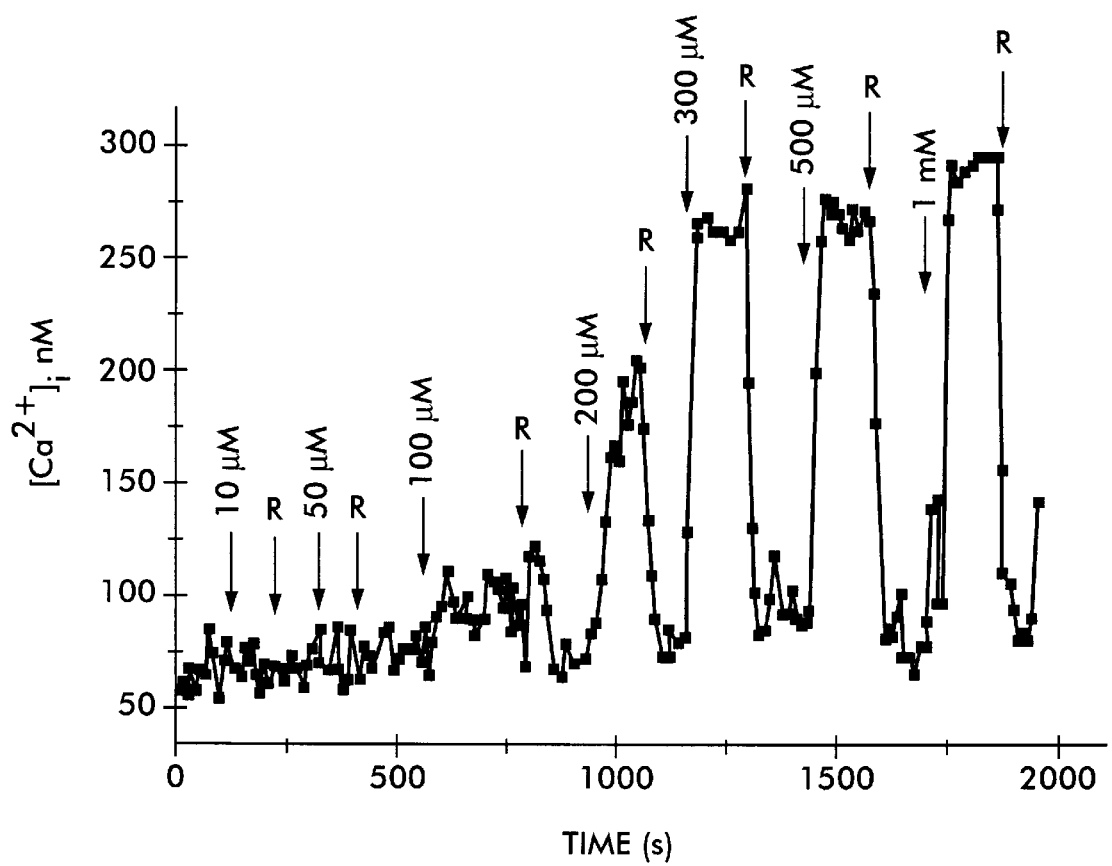
FIG. 2 shows an increase in intracellular calcium ion concentration in a human olfactory neuron by methyl o-aminobenzoate (MA) at concentrations of from about 10 $\mu$M to about 1 mM.
Figure 3:
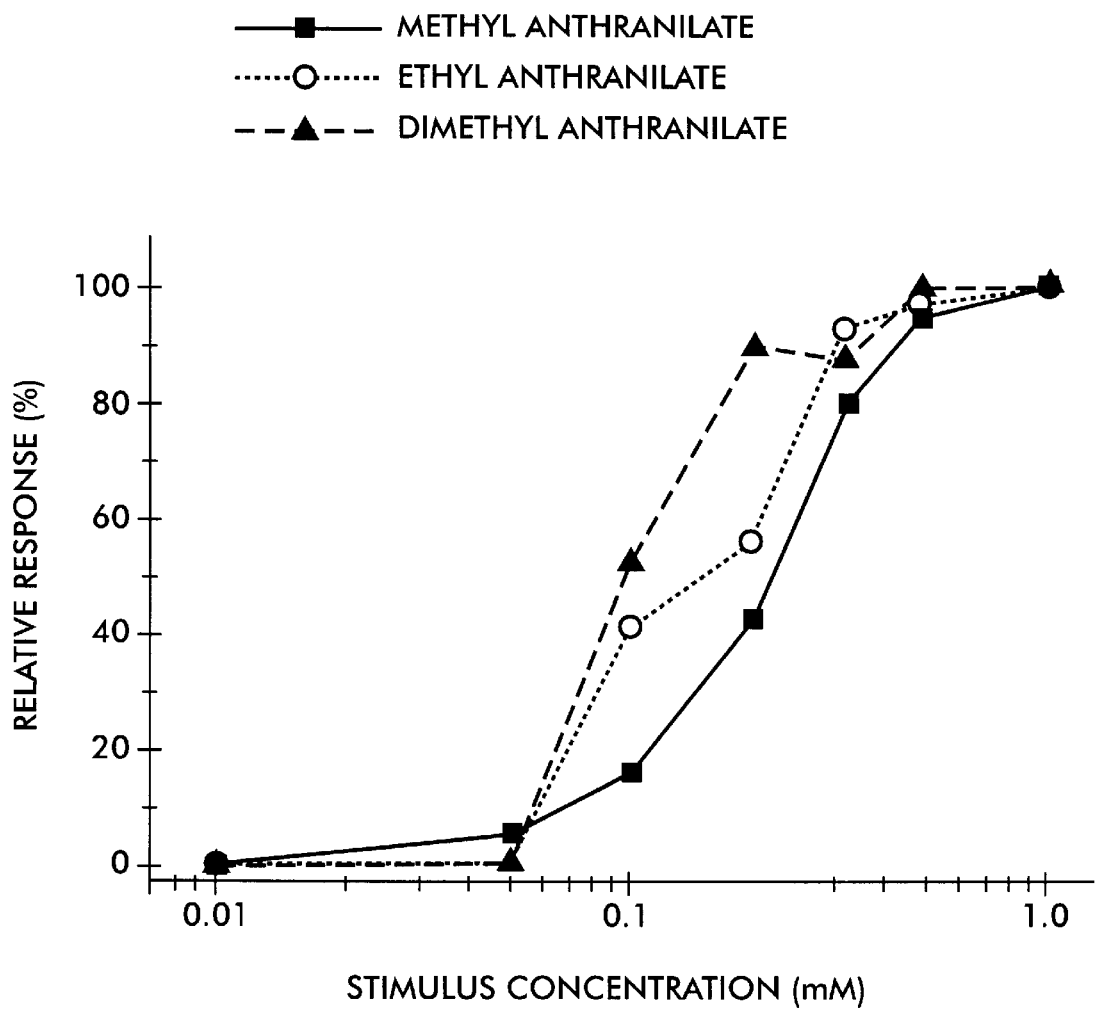
FIG. 3 shows relative effectiveness of different MA analogs in raising intracellular calcium in isolated human olfactory neurons. Cells were stimulated with methyl o-aminobenzoate (MA), ethyl o-aminobenzoate (ethyl anthranilate (EA)) and methyl o-N-methylaminobenzoate (dimethyl anthranilate (DMA)) at almost similar stimulation concentrations of from about 10 $\mu$M to about 1 mM.

Ringer's solutions containing methyl o-aminobenzoate (methyl anthranilate, MA) at 10 mM, 50 mM, 100 mM, 200 mM, 300 mM, 500 mM and 1 mM, respectively, were presented to olfactory cells prepared in the same manner as in Example 1, and the increase in the calcium ion concentration was determined in the same manner as in Example 1. The results are shown in FIG. 2. The relative response with concentration is depicted in FIG. 3.

Ethyl o-aminobenzoate (ethyl anthranilate (EA)), methyl o-N-methylaminobenzoate (methyl N-methyl anthranilate and dimethyl anthranilate (DMA)), and phenylpropyl o-aminobenzoate (phenylpropyl anthranilate (PPA)) were examined in a similar manner as described for MA above. The relative responses with increasing concentration for EA and DMA are also depicted in FIG. 3. The results indicate that DMA and EA are slightly more potent than MA.

Figure 4A:
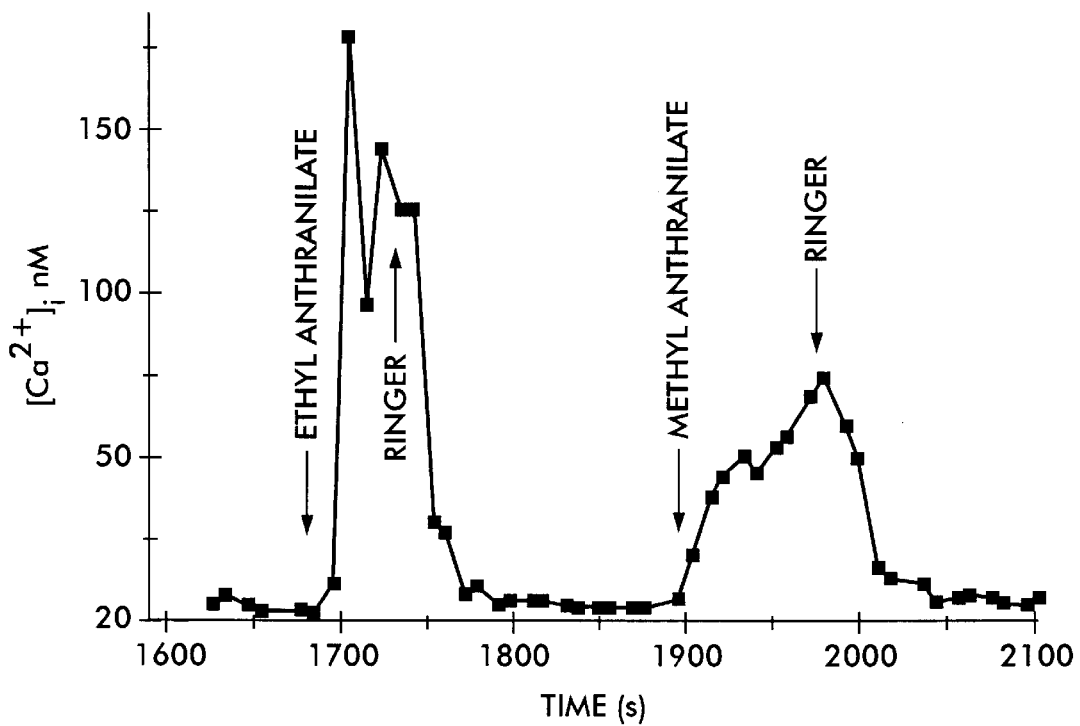
FIGS. 4 a–b show the change in calcium ion concentration over time using methyl o-aminobenzoate (MA), ethyl o-aminobenzoate (EA) and methyl o-N-methylanthranilate (DMA) at concentrations of 100 $\mu$M.
Figure 4B:
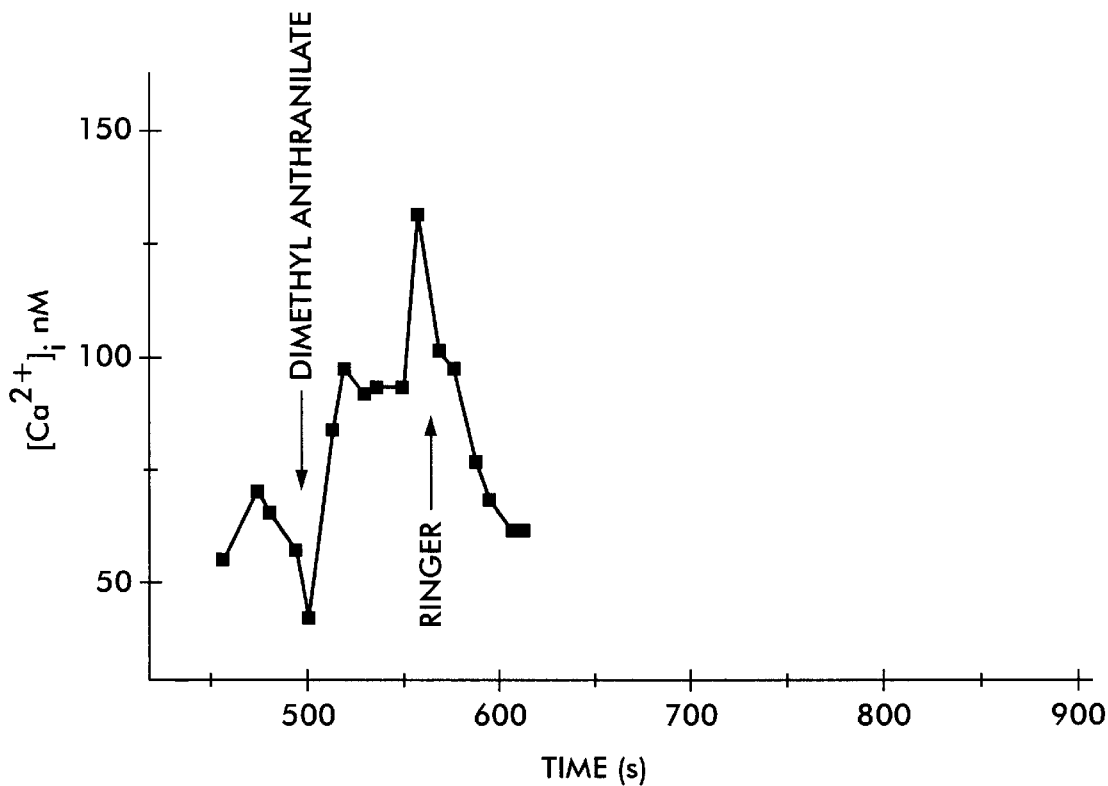
Figure 5:
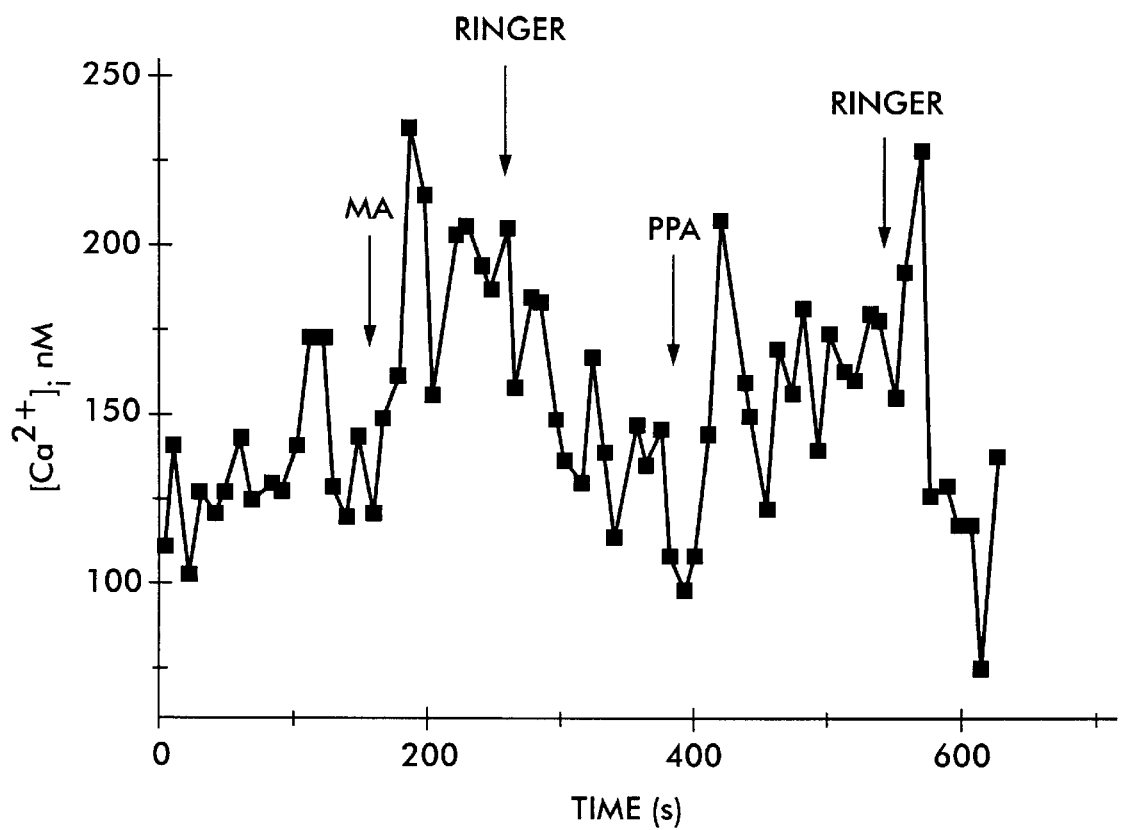
FIG. 5 shows the change in calcium ion concentration with time using MA and phenylpropyl o-aminobenzoate (phenyl propyl anthranilate (PPA)) at concentrations of 100 $\mu$M.

The increase in calcium ion concentration with time for each of EA, MA, DMA, and PPA is depicted in FIGS. 4 a–b and 5. Each compound was applied at 100 µM concentration, and the response of a different cell is shown in each graph. When the response was maximal (i.e., calcium concentrations leveled off), the compounds were washed out of the cell by applying Ringer's solution and the return of calcium concentrations to baseline levels was noted.

Example 3

Figure 6:
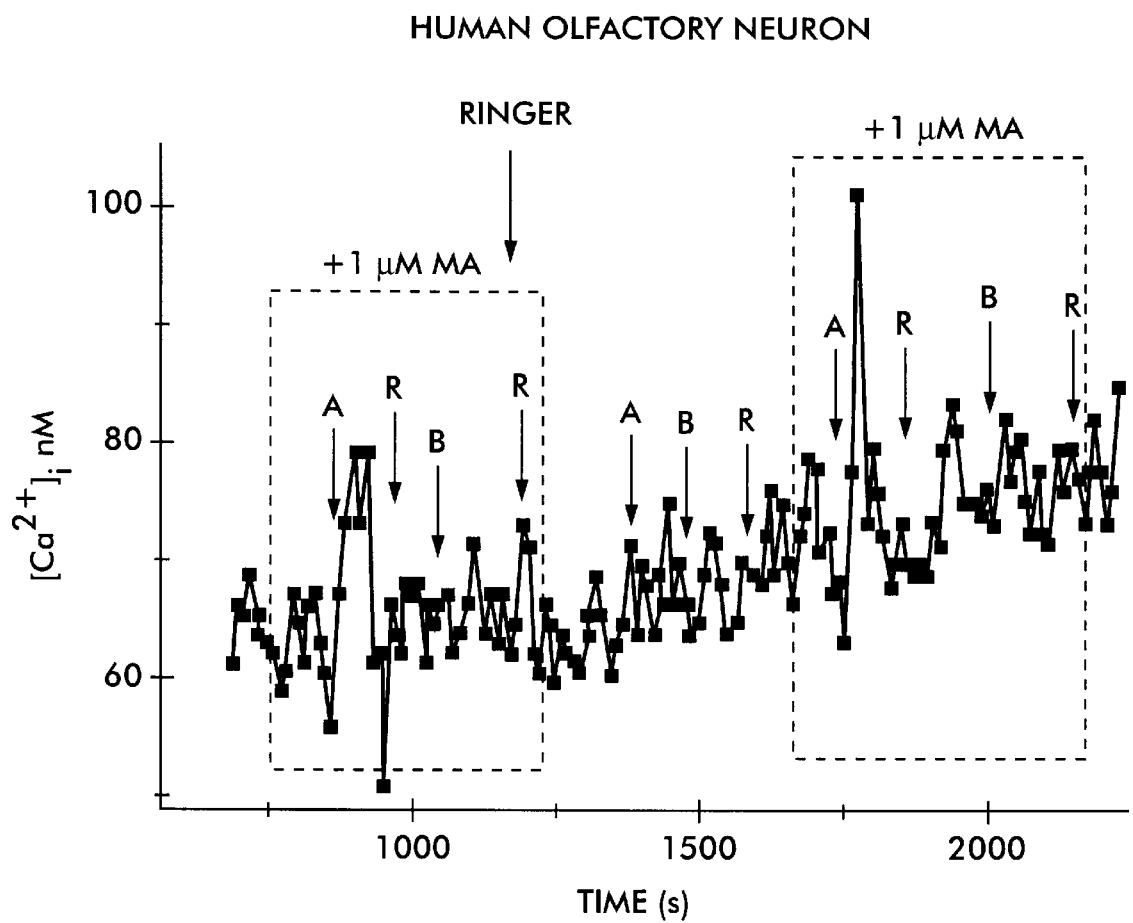
FIG. 6 shows the results obtained when Ringer's solution containing 1 $\mu$M methyl o-aminobenzoate (MA) in combination with odor-emitting substances Mix A or B (defined in Rawson et al., J. Neurosci. 77:1606–1613, 1977) was presented to olfactory cells.

A 1 mM concentration of methyl o-aminobenzoate (methyl anthranilate (MA)) in Ringer's solution was presented to some olfactory cells prepared in the same manner as described in Example 1 and the increase in the intracellular calcium ion concentration following the addition of the odor components Mix A or Mix B (Rawson et. al., *J. Neurophysiol.*, 77:1606–1613, 1997, incorporated herein by reference) was determined with time in the same manner as described in Example 2. The results are shown in FIG. 6. An increase in the calcium ion concentration was observed only in the case of Mix A. From this, it was found that, even at a concentration as low as 1 µM, MA can increase the calcium ion concentration when used in combination with another odor-emitting substance.

This particular cell did not respond to Mix B, indicating that this effect was not a non-specific effect on the cell membrane. Since human olfactory neurons from persons of 18–64 years of age respond to only one of the two mixes (either A or B, not both), this result show that the addition of MA merely enhanced the effectiveness of the odorant's activation of the transduction pathway that the cell possessed rather than stimulating an alternative odor detection and transduction pathway. This shows the specificity of this particular effect of MA to olfactory signal transduction pathways (Rawson et al., 1997).

Example 4

Figure 7:
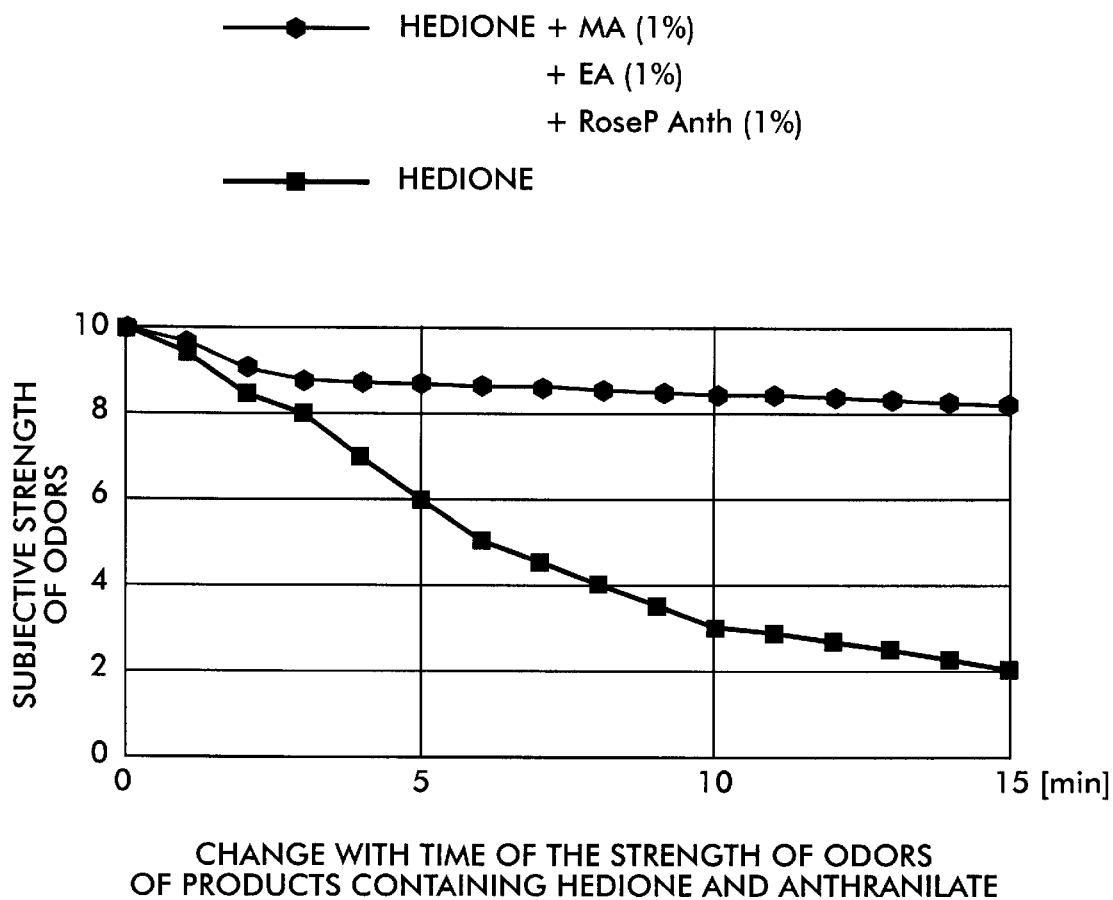
FIG. 7 shows the prevention of adaptation measured using a psychophysical approach in human subjects. The effect of adding 1% by weight of methyl anthranilate (MA), ethyl anthranilate (EA), and phenylethyl anthranilate (Rose PAnth) on adaptation to Hedione is shown.

Ten panels of human test subjects made functional evaluations in an adaptation test. The evaluation of the strength of odors was made using a visual analog scale that ranged from (0) no odor to (10) very strong odor. Test subjects were required to mark on the scale how intense the odors were. For example, if the odors were of moderate intensity they would mark a "5" on the scale. Such scaling is common in the sensory evaluation field (Stevens, S. S. *Psychophysics*, John Wiley & Sons, 1975). The strength of a continuous flow of Hedione (methyl dihydrojasmonate, Firmenich Ltd.), an odor-emitting substance, at a predetermined concentration was evaluated every 30 seconds for 15 minutes using the visual analog scale. Flow rate was 500 ml/min. Sample concentration was as follows: a 20 ml sample was introduced into 100 ml glass vessel and odor-free air was introduced at the above flow rate via an air tank, then via a glass vessel and through a Teflon tube into the nose. As depicted in FIG. 7, adaptation to the Hedione (squares) occurred within 5–10 minutes.

Methyl anthranilate, ethyl anthranilate, or phenyl ethyl anthranilate was then added at 1% by weight to the Hedione and tested as above. As can be seen from the results depicted in FIG. 7, adaptation had not yet occurred even after 15 minutes.

Example 5

Methylanthranilate (final concentration: 0.3% by weight) or a mixture of methyl anthranilate and ethylanthranilate (final concentration of each: 0.1% by weight) was added to a formulated perfume (ST-AD) adapts normally and tested as described in Example 4.

The composition of the formulated perfume (ST-AD) was as follows:

| Compound | Percent |
| --- | --- |
| Jasmal (3-amuyl-4-acetoxytetrahydropyran, produced by IFF) | 10.0 |
| Florapal (acetaldehyde 2-phenyl 2,4-pentanediol acetal, produced by H&R) | 10.0 |
| Cantoxal (2-methyl-3(p-methoxy-phenyl) propanal, produced by IFF) | 10.0 |
| Rosephenone 10% (trichloromethyl-phenyl carbinyl acetate, produced by Toyotama Corporation) | 10.0 |
| Cycraprop (tricyclodecnyl proprionate produced IFF) | 10.0 |
| Ethyl vanillin 10% | 5.0 |
| Galaxolide 50 BB (hexahydrohexamethylcyclopenta-γ-pyran, produced by IFF) | 10.0 |
| Kovanol (4-hydroxy-4-methylpentyl-3-cyclohexane carbaldehyde, produced by Takasago International Corporation) | 15.0 |
| Woodyfrol (acetyl cedrene, produced by Takasago International Corporation) | 10.0 |
| OTBCHA (o-tert-butylcyclohexyl acetate) | 10.0 |

Figure 8:
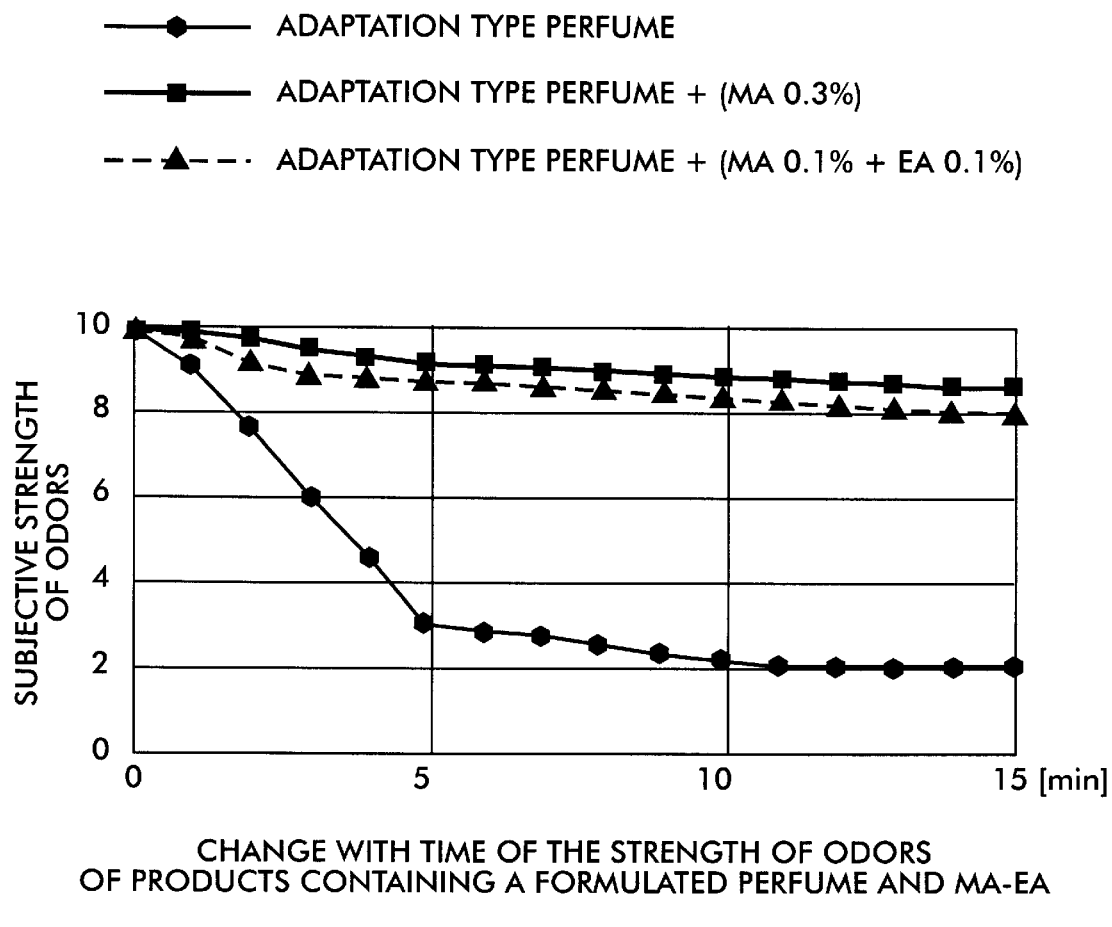
FIG. 8 shows the prevention of adaptation to a complex adaptation-type perfume (ST-AD) by adding MA, or MA and EA.

The results are depicted in FIG. 8. As depicted therein, adaptation to formulated perfume ST-AD was prevented for at least 15 minutes. Further, while 0.3% methyl anthranilate was necessary for single use, a combination concentration of methyl anthranilate and ethyl anthranilate as low as 0.2% by weight in total showed the equivalent effect.

Example 6

The adjuvants of the present invention can be used in a variety of formulations. Some examples follow. Although specific aminobenzoates are listed in the formulations, any of the following can be used: methyl anthranilate, methyl N-methyl anthranilate, ethyl anthranilate, benzyl anthranilate, phenylethyl anthranilate, or phenylpropyl anthranilate.

| | 1) Emollient Cream | |
| --- | --- | --- |
| Component | Compound | Percent |
| (A) | stearic acid | 2.0 |
| | ethyl anthranilate | 2.0 |
| | stearyl alcohol | 7.0 |
| | cetanol | 4.0 |
| | Sucuwarane | 10.0 |
| | polyoxyethylene cetyl ether (25 E.O.) | 3.0 |
| | glyceryl monostearate | 2.0 |

-continued

| 1) Emollient Cream | | |
|---|---|---|
| Component | Compound | Percent |
| | 1,3-buthylene glycol | 7.0 |
| | perfume | 0.5 |
| (B) | purified water | 62.5 |

(A) was dissolved and heated at 80° C. (B) was heated at 80° C. and mixed with (A) and the mixture was emulsified and removed at 35° C. while stirring, and formed into a product.

| 2) Cosmetic water | |
|---|---|
| Compound | Percent |
| glycerin | 5.0 |
| polyoxyethylene sorbitan monolaurate (20 E.O.) | 1.5 |
| 95% ethanol | 5.0 |
| methyl N-methyl anthranilate | 0.5 |
| preservative | suitable amount |
| perfume | suitable amount |
| pigment | suitable amount |
| purified water | 88.0 |

The above ingredients were mixed uniformly and stirred into a product.

| 3) Emulsion | | |
|---|---|---|
| Component | Compound | Percent |
| (A) | squalane | 8.0 |
| | vaseline | 2.0 |
| | beeswax | 1.0 |
| | sorbitan sesquioleate | 1.0 |
| | polyoxyethylene oleyl ether (20 E.O.) | 2.0 |
| | benzyl anthranilate | 1.0 |
| | perfume | 0.2 |
| (B) | potassium hydroxide | 0.1 |
| | carboxyvinyl polymer | 0.2 |
| | glycerin | 5.0 |
| | purified water | 72.5 |
| (C) | 95% ethanol | 7.0 |

The emulsion is prepared by mixing these compounds in a glass vessel.

| 4) Bath Powder | |
|---|---|
| Compound | Percent |
| sodium sulfate anhydrous | 63.5 |
| sodium bicarbonate | 30.0 |
| sylysia (Fuji Sylesia) | 0.5 |
| uranine yellow (1% in sodium sulfate anhydrous | 5.0 |
| ethyl anthranilate | 0.2 |
| perfume | 0.1 |

The above ingredients are mixed uniformly and formed into a product.

All references cited herein are hereby incorporated by reference in their entireties.

What is claimed is:

1. A method for preventing adaptation to an odor-emitting substance in a subject, said method comprising combining an effective amount of an adjuvant comprising one or more compounds of the following formula (1):

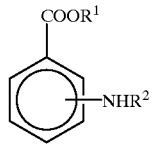

wherein R1 is a C1 to C8 lower alkyl group or a C7 to C9 aralkyl group, and R2 is a hydrogen atom or a C1 to C8 lower alkyl group, with said odor-emitting substance, wherein said adjuvant prolongs the sensory response to said odor-emitting substance upon contact to said adjuvant-containing odor-emitting substance by said subject.

2. The method according to claim 1, wherein the subject is selected from the group consisting of mammals, birds, reptiles, fishes, and amphibians.

3. The method according to claim 1 wherein the odor-emitting substance is a perfume.

4. The method according to claim 1 wherein the odor-emitting substance is harmful substance.

* * * * *